(12) United States Patent
Koizumi et al.

(10) Patent No.: US 8,101,797 B2
(45) Date of Patent: Jan. 24, 2012

(54) PROCESS FOR PRODUCING METHIONINE

(75) Inventors: Yoshiyuki Koizumi, Ehime (JP); Akinori Goto, Ehime (JP); Takushi Azemi, Ehime (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/613,568

(22) Filed: Nov. 6, 2009

(65) Prior Publication Data
US 2010/0121102 A1    May 13, 2010

(30) Foreign Application Priority Data
Nov. 7, 2008 (JP) .................................. 2008-287059

(51) Int. Cl.
*C07C 323/03* (2006.01)
(52) U.S. Cl. ........................................................ 562/559
(58) Field of Classification Search ........................ None
See application file for complete search history.

(56) References Cited

U.S. PATENT DOCUMENTS

| 4,069,251 A | 1/1978 | Mannsfeld et al. |
| 4,303,621 A | 12/1981 | Lussling et al. |
| 5,945,563 A | 8/1999 | Imi et al. |
| 2007/0055078 A1 | 3/2007 | Shiozaki et al. |

FOREIGN PATENT DOCUMENTS

| EP | 0839804 A2 | 5/1998 |
| EP | 1760074 A1 | 3/2007 |
| JP | 51-1415 A | 1/1976 |
| JP | 54-9174 B2 | 4/1979 |
| JP | 05-320124 A | 12/1993 |
| JP | 2007-63141 A | 3/2007 |

*Primary Examiner* — Paul A Zucker
(74) *Attorney, Agent, or Firm* — Panitch Schwarze Belisario & Nadel LLP

(57) ABSTRACT

A process for producing methionine advantageously in view of cost, while efficiently recovering useful components, is provided including the following steps: (1) hydrolyzing 5-[2-(methylthio)ethyl]imidazolidine-2,4-dione in the presence of a basic potassium compound; (2) introducing carbon dioxide into the reaction solution obtained in the step (1) to thereby precipitate methionine, and separating the resulting slurry into a precipitate and a mother liquor; (3) concentrating the mother liquor obtained in the step (2), mixing the resulting concentrate with a lower alcohol, introducing carbon dioxide into the resulting mixture to thereby precipitate methionine and potassium hydrogencarbonate, and separating the resulting slurry into a precipitate and a mother liquor; and (4) concentrating the mother liquor obtained in the step (3), treating the resulting concentrate by heating at a temperature of from 150 to 200° C., and recycling the treated solution for use in step (2).

4 Claims, No Drawings

PROCESS FOR PRODUCING METHIONINE

BACKGROUND OF THE INVENTION

1. Field of the Invention

This application was filed claiming Paris Convention priority of Japanese Patent Application No. 2008-287059, the entire content of which is herein incorporated by reference.

The present invention relates to a process for producing methionine by a hydrolysis reaction of 5-[(2-(methylthio)ethyl)]imidazolidine-2,4-dione [refer to the following reaction formula (1)]. Methionine is useful as an additive to feeds for animals.

[Chemical formula 1]

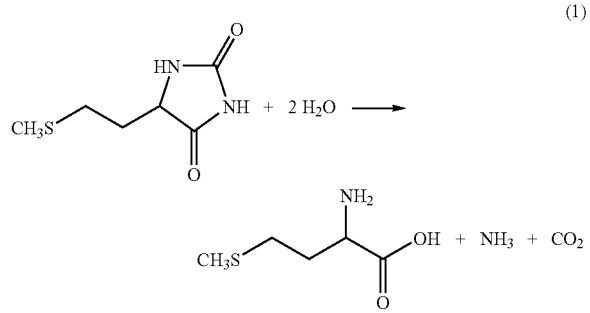

(1)

2. Description of the Related Art

The following process is known as one of processes for producing methionine: that is, 5-[(2-(methylthio)ethyl)]imidazolidine-2,4-dione is hydrolyzed under a basic condition, using a basic potassium compound such as potassium carbonate or potassium hydrogencarbonate, to thereby produce methihonine. In this process, carbon dioxide is introduced into the reaction solution obtained after the hydrolysis, to thereby cause crystallization, so that methionine is separated and obtained as crystals. The mother liquor obtained after the separation of methionine still contains methionine at a concentration equivalent to a solubility and also contains potassium hydrogencarbonate which can be recycled as the above-described basic potassium compound. This mother liquor, therefore, should be recycled for use in the above-described hydrolysis reaction. In this step, when the entire amount of the mother liquor is recycled, impurities tend to accumulate, and therefore, the mother liquor is needed to be purged of at a given rate. To treat the mother liquor thus purged of as liquid-waste leads to a loss of methionine and potassium hydrogencarbonate contained in the mother liquor, and a cost for the treatment of liquid-waste is considerably high. Therefore, this method is not advisable.

Under such a circumstance, there are reported many methods for recovering, from mother liquors as described above, methionine and potassium hydrogencarbonate as so-called second crystals. For example, the following method is disclosed in JP-B-54-9174: the above-described mother liquor is mixed with a water-soluble solvent such as an alcohol (e.g., methyl alcohol) or acetone; and then, carbon dioxide is introduced into the resulting mixture to cause crystallization. The following method is also disclosed in JP-A-51-1415: the above-described mother liquor is concentrated; and then, carbon dioxide is introduced into the resulting concentrate to cause crystallization. The following method is further disclosed in JP-A-5-320124: the above-described mother liquor is mixed with isopropyl alcohol; and then, carbon dioxide is introduced into the resulting mixture to cause crystallization.

The following method is further disclosed in JP-A-2007-63141: the above-described mother liquid obtained after the separation of the first crystals is concentrated; then, the resulting concentrate is subjected to a heat treatment at 165° C.; then, the treated solution is mixed with isopropyl alcohol; and then, carbon dioxide is introduced into the resulting mixture to cause crystallization. This Patent Publication also discloses a method of recovering methionine as the third crystals as follows: the mother liquor obtained after the separation of the second crystals is concentrated; and carbon dioxide is introduced into the resulting concentrate to cause crystallization.

SUMMARY OF THE INVENTION

An object of the present invention is to provide a cost-effective process for producing methionine while efficiently recovering useful components.

The present inventors made the following trial: that is, the mother liquor obtained after the separation of the second crystals was concentrated, and then, the resulting concentrate was recycled for use in the first crystallization step. However, the filtration rate for separation became poor, with the result that the volume density of the separated methionine became lower, which led to a higher production cost.

As a result of the present inventors' further studies, it is found that the amount of methionine dipeptide in the mother liquor obtained after the separation of the second crystals gives an influence on the volume density of the separated methionine: in other words, when the amount of methionine dipeptide is large, the crystallinity of methionine obtained by the crystallization becomes poor, so that the filtration thereof becomes hard, with the result that the volume density of the separated methionine becomes lower. Then, based on this finding, the mother liquor obtained after the separation of the second crystals was concentrated; and then, the resulting concentrate was treated by heating to hydrolyze methionine dipeptide and convert the same into methionine; and after this step, the resulting mother liquor was recycled for use in the first crystallization step. By doing so, it is found that the crystallinity of methionine obtained by the crystallization was improved, so that the filtration rate of methionine was remarkably improved, which leads to a higher volume density of the separated methionine. The present invention is accomplished based on this finding.

The present invention provides the following:

[1] A process for producing methionine, comprising the following steps (1), (2), (3) and (4):

(1) a reaction step of hydrolyzing 5-[2-(methylthio)ethyl]imidazolidine-2,4-dione in the presence of a basic potassium compound;

(2) a first crystallization step of introducing carbon dioxide into the reaction solution obtained in the step (1) to thereby precipitate methionine, and separating the resulting slurry into a precipitate and a mother liquor;

(3) a second crystallization step of concentrating the mother liquor obtained in the step (2), mixing the resulting concentrate with a lower alcohol, introducing carbon dioxide into the resulting mixture to thereby precipitate methionine and potassium hydrogencarbonate, and separating the resulting slurry into a precipitate and a mother liquor; and (4) a heating step of concentrating the mother liquor obtained in the step (3), treating the resulting concentrate by heating at a temperature of from 150 to 200° C., and recycling the resulting treated solution for use in the step (2).

[2] The process defined in the above item [1], wherein the lower alcohol used in the step (3) is selected from methyl alcohol, ethyl alcohol, n-propyl alcohol, isopropyl alcohol and t-butyl alcohol.

[3] The process defined in the above item [1] or [2], wherein the heat treatment is continued for 0.3 to 10 hours in the step [4].

According to the present invention, the filtration rate in the first crystallization step after the recycling is improved, and the volume density of the separated methionine becomes higher, so that the recovery of the first crystals can be efficiently carried out, with the result that methionine can be produced advantageously in view of cost.

DETAILED DESCRIPTION OF THE INVENTION

In the present invention, 5-[2-(methylthio)ethyl]-imidazolidine-2,4-dione is used as a stating material, which is hydrolyzed in the presence of a basic potassium compound, to thereby obtain a reaction solution containing methionine as a potassium salt [the reaction step (1)]. For example, the starting material, i.e., 5-[2-(methylthio)ethyl]imidazolidine-2,4-dione, can be prepared by reacting 2-hydroxy-4-methylthiobutanenitrile with ammonia and carbon dioxide, or with ammonium carbonate [refer to the following reaction formula (2) or (3)].

[Chemical formula 2]

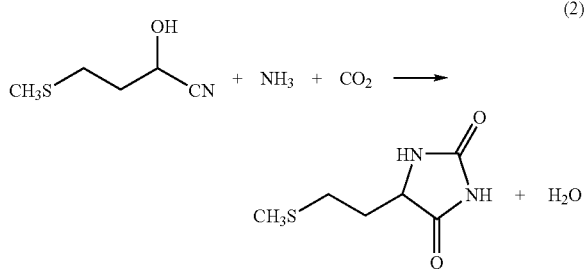

(2)

[Chemical formula 3]

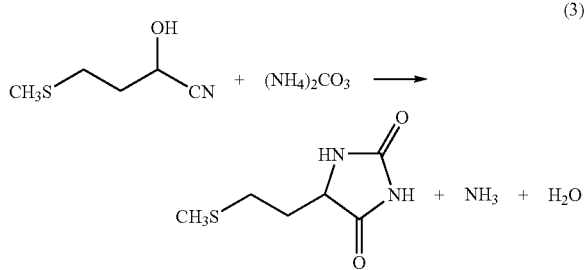

(3)

Examples of the basic potassium compound include potassium hydroxide, potassium carbonate, potassium hydrogencarbonate, etc. Two or more selected therefrom optionally may be used in combination. The amount of the basic potassium compound to be used is usually from 2 to 10 equivalents, preferably from 3 to 6 equivalents, in terms of potassium, per one equivalent of 5-[2-(methylthio)-ethyl]imidazolidine-2,4-dione. The amount of water to be used is usually 2 to 20 times larger in weight than that of 5-[2-(methylthio)ethyl]imidazolidine-2,4-dione.

Preferably, the hydrolysis reaction is carried out under a gauge pressure of from about 0.5 to about 1 MPa, by heating the starting material to a temperature of from about 150 to about 200° C. The reaction time is usually from 10 minutes to 24 hours.

To obtain methionine from the hydrolysis reaction solution thus obtained, carbon dioxide is introduced into the reaction solution to cause crystallization, and the resulting slurry is separated into a precipitate and a mother liquor by filtration or decantation, to thereby obtain the precipitated methionine as the first crystals [the first crystallization step (2)].

The reaction solution is allowed to absorb carbon dioxide by the introduction of carbon dioxide, so that a potassium salt of methionine is precipitated as free methionine.

Preferably, the introduction of carbon dioxide is carried out under a gauge pressure of usually from 0.1 to 1 MPa, preferably from 0.2 to 0.5 MPa.

The crystallization temperature is usually from 0 to 50° C., preferably from 10 to 30° C. The crystallization time may be determined based on a period of time during which the carbon dioxide saturates in the hydrolysis reaction solution to sufficiently precipitate methionine, and it is usually from 30 minutes to 24 hours.

If needed, the separated methionine is washed or adjusted in pH, and then is dried to obtain a product. Preferably, the drying is carried out by heating at about 50 to about 120° C. under a slightly reduced pressure. The drying time is usually from 10 minutes to 24 hours.

The mother liquor obtained after the separation of methionine (hereinafter referred to as "a first crystallization mother liquor") still contains methionine at a concentration equivalent to solubility, and also contains potassium hydrogencarbonate which can be recycled as the above-described basic potassium compound. Accordingly, it is desirable to recycle the first crystallization mother liquor for use in the hydrolysis reaction in the step (1). In the meantime, this mother liquor contains impurities, e.g., amino acids such as glycine and alanine, other than methionine, and a coloring component, attributed to the impurities in the stating material or the side reaction of the hydrolysis. Therefore, these impurities are brought into a hydrolysis reaction by recycling the mother liquor. To avoid this disadvantage, it is needed to recycle the first crystallization mother liquor in such an amount that these impurities are not allowed to accumulate, but not the entire amount thereof. The proportion of the first crystallization mother liquor to be recycled is usually from 50 to 90% by weight, preferably from 70 to 90% by weight, based on the entire weight of the first crystallization mother liquor.

Prior to the recycling of the first crystallization mother liquor, desirably, the same mother liquor is concentrated, and the resulting concentrate is used as a recycled solution. By this concentration, carbon dioxide is distilled off from the first crystallization mother liquor, and thus, a recycled solution with an increased basic property, advantageous for the hydrolysis reaction, can be obtained. Also, the concentration carried out at so high a temperature as from 100 to 140° C. is effective to facilitate a reaction for converting potassium hydrogencarbonate in the mother liquor, into potassium carbonate ($2KHCO_3 \rightarrow K_2CO_3 + H_2O + CO_2$), so that a recycled solution with a further increased basic property, advantageous for the hydrolysis reaction, can be obtained. While this concentration may be done under an atmospheric pressure, a reduced pressure or a raised pressure, it is effective to employ a pressurizing condition in order to carry out the concentration at a high temperature as described above. The concentration ratio is usually from 2- to 4-fold, preferably from 1.5- to 3.5-fold. In this regard, the concentration ratio means a ratio of the weight of the solution before concentration thereof to the weight of the same solution after the concentration thereof (the weight of the solution before concentration thereof/the weight of the same solution after the concentration thereof), and this term means the same, unless otherwise specified.

A portion of the first crystallization mother liquor (concentrated), which is not recycled, is crystallized so as to recover therefrom methionine and potassium hydrogencarbonate as second crystals. In the present invention, this crystallization is allowed to take place by introducing carbon dioxide into a mixture of the concentrated first crystallization mother liquor with a lower alcohol, and the resulting slurry is separated into a precipitate and a mother liquor by filtration or decantation, so that the precipitated methionine and potassium hydrogencarbonate are recovered as the second crystals [the second crystallization step (3)]. In this connection, the concentrated first crystallization mother liquor may be entirely subjected to this crystallization, without recycling the same.

As the lower alcohol, any of alkyl alcohols each having a $C_{1-5}$ alkyl group is usually used. Preferable among those is an alkyl alcohol which can be admixed with water at an optional ratio, such as methyl alcohol, ethyl alcohol, n-propyl alcohol, isopropyl alcohol or t-butyl alcohol, among which isopropyl alcohol is particularly preferred. The amount of the lower alcohol to be used is usually 0.05 to 5 times, preferably 0.1 to 2 times larger in weight than the amount of the first crystallization mother liquor to be subjected to crystallization. The mixing of the first crystallization mother liquor with the lower alcohol may be done before the introduction of carbon dioxide or simultaneously with the introduction of carbon dioxide.

The first crystallization mother liquor to be subjected to the second crystallization is concentrated, as well as the first crystallization mother liquor to be recycled. By this concentration, the recovery of the second crystals can be improved. This concentration may be carried out under the same conditions as those for the concentration of the first crystallization mother liquor to be recycled; or otherwise, the entire amount of the first crystallization mother liquor may be concentrated, and then may be divided into a portion for recycling and a portion for the second crystallization.

During the concentration of the first crystallization mother liquor, the basic property of the mother liquor is enhanced, so that the free methionine formed by the conversion in the first crystallization step is again formed into a potassium salt of methihonine. Accordingly, also in the second crystallization step, carbon dioxide is introduced into a mixture of the concentrated first crystallization mother liquor with a lower alcohol to thereby convert the potassium salt of methionine into free methionine.

Preferably, the concentrated mother liquor is subjected to a heat treatment. By doing so, methionine dipeptide (a dehydro-condensation product of two methionine molecules) contained in the mother liquor is hydrolyzed to facilitate reproduction of methionine. Preferably, this heat treatment is carried out at a temperature of from about 140 to about 180° C. under a gauge pressure of 0.5 to 2 MPa, and the heat-treating time is usually from 10 minutes to 24 hours.

The introduction of carbon dioxide is done under a gauge pressure of usually from 0.1 to 1 MPa, preferably from 0.2 to 0.5 MPa, as well as that in the first crystallization step.

The crystallization temperature is usually from 0 to 50° C., preferably from 5 to 20° C. The crystallization time may be selected based on a period of time during which carbon dioxide saturates in the above-described solution mixture to sufficiently precipitate methionine and potassium hydrogencarbonate, and it is usually from 10 minutes to 24 hours.

Preferably, the recovered second crystals (a mixture of methionine and potassium hydrogencarbonate) is recycled for use in the hydrolysis reaction in the step (1). In this regard, from the viewpoint of operating efficiency, it is preferable to dissolve the second crystals in the first crystallization mother liquor to be recycled, and to recycle the resulting solution.

The mother liquor obtained after the separation of the second crystals (hereinafter referred to as "a second crystallization mother liquor") still contains methionine and potassium hydrogencarbonate. In the present invention, methionine and potassium hydrogencarbonate are further recovered from the second crystallization mother liquor, by concentrating the second crystallization mother liquor, subjecting the concentrated second crystallization mother liquor to a heat treatment [the heating step (4)], and recycling the treated solution for use in the first crystallization step (2) to thereby recover methionine and potassium hydrogencarbonate.

By concentrating the second crystallization mother liquor, the recovery of methionine is improved. This concentration may be carried out under the same conditions as those for the concentration of the first crystallization mother liquor to be recycled.

By the heat treatment following the concentration, methionine dipeptide contained in the mother liquor is hydrolyzed to thereby facilitates reproduction of methionine. This heat treatment is carried out at a temperature of from 150 to 200° C., preferably from 160 to 180° C., under a gauge pressure of from about 0.5 to about 2 MPa. The heat-treating time is preferably from 0.3 to 10 hours, more preferably from 0.5 to 5 hours.

Preferably, this heat treatment is continued until the ratio of methionine dipeptide to methionine reaches preferably 5 to 50% by weight, more preferably 5 to 40% by weight.

The entire amount of the second crystallization mother liquor may be concentrated and subjected to the heat treatment, and the resulting treated solution may be recycled for use in the first crystallization step (2); or otherwise, a part of the second crystallization mother liquor may be concentrated and subjected to the heat treatments and then may be recycled for use in the first crystallization step (2).

Also, during the concentration of the second crystallization mother liquor, the basic property of the mother liquor is enhanced, so that the free methionine formed by the conversion in the second crystallization step is again formed into a potassium salt of methihonine. Accordingly, carbon dioxide is introduced into a mixture of the concentrated and heat-treated second crystallization mother liquor with the hydrolyzed solution to thereby convert the potassium salt of methionine, into free methionine.

All of the foregoing steps (1) to (4) may be conducted by either a continuous process or a batch process; or otherwise, some of these steps may be conducted by a continuous process, and other steps may be conducted by a batch process.

In the present invention, by recycling the concentrated and heat-treated second crystallization mother liquor for use in the first crystallization step (2), a wet cake content in the first crystallization step reaches 5 to 30%, particularly 10 to 25%, which leads to an improved filtration rate. Also, the volume density of the separated methionine becomes so high as 0.3 to 0.6 g/cc, particularly 0.4 to 0.5 g/cc.

EXAMPLES

Next, Examples of the present invention will be illustrated. The scope of the present invention, however, is not limited to them in any way. In Examples, % and part as units of concentration and amounts are based on weight, unless otherwise specified.

Example 1

Reaction Step (1)

A hydrolysis reaction was carried out at a temperature of from 173 to 178° C. for a residence time of one hour under a gauge pressure of 0.88 MPa, while introducing, into a reactor, an aqueous solution containing 5-[2-(methylthio)ethyl]imidazolidine-2,4-dione at a concentration of 18.7% (100 parts per hour), potassium hydroxide (1.0 part per hour), a primary concentrated solution (methionine concentration: 6.0%, and potassium concentration: 13.5%) of a first crystallization mother liquor separately prepared (67.6 parts per hour), and a solution containing second crystals separately prepared (methionine concentration: 7.6%, and potassium concentration: 18.2%, i.e., a concentrated solution of a second crystallization wet cake dissolved in the concentrated first crystallization mother liquor) (25.8 parts per hour).

First Crystallization Step (2)

A reaction solution (133.1 parts per hour) obtained by the above-described hydrolysis reaction was mixed with water (60.7 parts per hour) and polyvinyl alcohol (0.023 part per hour), and the resulting mixture was introduced into a crystallizer and was crystallized therein at 20° C. under a gauge pressure of 0.3 MPa by carbon dioxide, to precipitate methionine. The resulting slurry was filtered, and the residue was washed with water and was then dried at a temperature of from 85 to 105° C. under a slightly reduced pressure, to thereby obtain methionine (15.6 parts per hour) (purity: 99.6%, and yield: 97%). Also, a first crystallization mother liquor (184.0 parts per hour) was recovered as the filtrate.

The first crystallization mother liquor (184.0 parts per hour) was introduced into a concentrator and was concentrated therein at 115° C. and then at 140° C. under a gauge pressure of 0.2 MPa, to thereby obtain a primary concentrated solution (106.4 parts per hour) (primary concentration ratio: 1.7-fold). This primary concentrated solution was analyzed, and the following were found: methionine concentration: 6.0%; potassium concentration: 13.5%; and a ratio of methionine dipeptide to methionine: 36.5%.

A portion (67.6 parts per hour) of the primary concentrated solution (106.4 parts per hour) of the above-described first crystallization mother liquor was recycled for use in a hydrolysis reaction as described above. A portion (18.5 parts per hour) of the primary concentrated solution was introduced into a heater and was treated therein by heating at 165° C. under a gauge pressure of 1 MPa for a residence time of one hour. After that, the heat-treated solution was introduced into a concentrator and was concentrated therein at 135° C. under a gauge pressure of 0.2 MPa, to obtain a secondary concentrated solution (12.3 parts per hour) (secondary concentration ratio: 1.5-fold, and overall concentration ratio of the primary and secondary concentrations: 2.6-fold). The remaining portion (20.3 parts per hour) of the primary concentrated solution was used to dissolve a second crystallization wet cake described below.

Second Crystallization Step (3)

The secondary concentrated solution (12.3 parts per hour) of the above-described first crystallization mother liquor was mixed with isopropyl alcohol (3.3 parts per hour), and the resulting mixture was introduced into a crystallizer and was crystallized therein at a temperature of from 12 to 16° C. under a gauge pressure of 0.3 MPa by carbon dioxide. The resulting slurry was filtered to obtain a second crystallization wet cake (7.8 parts per hour) as the residue. Also, a second crystallization mother liquor (9.1 parts per hour) was recovered as the filtrate.

The second crystallization wet cake (7.8 parts per hour) was dissolved in the remaining portion (20.3 parts per hour) of the primary concentrated solution of the above-described first crystallization mother liquor, and the resulting solution was introduced into a concentrator and was concentrated therein at 80° C. under an atmospheric pressure, to thereby distill off isopropyl alcohol contained in the second crystals, so that a solution of the second crystals (25.8 parts per hour) was obtained. This solution of the second crystals was analyzed, and the following were found: methionine concentration: 7.6%, and potassium concentration: 18.2%. This solution of the second crystals (25.8 parts per hour) was recycled for use in the above-described hydrolysis reaction.

Heating Step (4)

The above-described second crystallization mother liquor (9.1 parts per hour) was introduced into a concentrator and was concentrated therein at a temperature from 80 to 110° C. under an atmospheric pressure, to thereby distill off isopropyl alcohol, so that a primary concentrated solution (6.0 parts per hour) (primary concentration ratio: 1.5-fold) was obtained. This primary concentrated solution was analyzed, and the following were found: methionine concentration: 3.14%; potassium concentration: 7.25%; and a ratio of methionine dipeptide to methionine: 102.9%.

A portion of the primary concentrated solution of the second crystallization mother liquor was introduced into a concentrator and was concentrated therein at 60° C. under a reduced pressure (an absolute pressure of 60 mmHg (8 kPa)) until the secondary concentration ratio reached 2.3-fold (overall concentration ratio of the primary and secondary concentrations: 3.5-fold). This secondary concentrated solution was analyzed, and the following were found: glycine concentration: 0.69%, and alanine concentration: 1.07%.

The secondary concentrated solution was poured in a heater and was heated therein at 180° C. for one hour. The heated solution was analyzed, and the following were found: methionine concentration: 10.39%; methionine dipeptide concentration: 3.72%; and a ratio of methionine dipeptide to methionine: 35.8%.

The above-described heated solution (1.9 parts per hour) and the reaction solution (133.1 parts per hour) obtained by the above-described hydrolysis reaction were mixed with water (60.7 parts per hour) and polyvinyl alcohol (0.023 part per hour), and the resulting mixture was introduced into a crystallizer and was crystallized therein at 20° C. under a gauge pressure of 0.3 MPa by carbon dioxide, to thereby precipitate methionine. The resulting slurry was filtered, and the residue was washed with water. The resulting residue had a wet cake content of 20%. This wet cake was dried at a temperature of from 85 to 105° C. under a slightly reduced pressure, to obtain methionine (17.1 parts per hour) (purity: 99.6%, and yield: 97%). The volume density of this methionine was 0.46 g/cc.

Comparative Example 1

The secondary concentrated solution (1.9 parts per hour) of the second crystallization mother liquor obtained in Example 1 and the reaction solution (133.1 parts per hour) obtained by the above-described hydrolysis reaction were mixed with water (60.7 parts per hour) and polyvinyl alcohol (0.023 part per hour), and the resulting mixture was introduced into a crystallizer and was crystallized therein at 20° C. under a gauge pressure of 0.3 MPa by carbon dioxide, to thereby precipitate methionine. The resulting slurry was filtered, and the residue was washed with water. The resulting residue had a wet cake content of 56%. This wet cake was dried at a temperature of from 85 to 105° C. under a slightly reduced pressure, to obtain methionine (17.1 parts per hour) (purity: 99.6%, and yield: 97%). The volume density of this methionine was 0.22 g/cc.

Method of Measuring Volume Density

The methionine powder after dried was gently poured into a 50 cc measuring cylinder, and the weight W (g) and the volume (V) (cc) thereof were measured, without tapping the cylinder. The volume density of the methionine powder was calculated by the following equation:

$$\text{Volume density (g/cc)} = W/V.$$

According to the present invention, the filtration rate of slurry in the first crystallization step after recycling is improved, and the volume density of the separated methionine is increased. Therefore, the first crystals are efficiently recovered, and methionine can be produced advantageously in view of cost.

What is claimed is:

1. A process for producing methionine, comprising the following steps (1), (2), (3) and (4):
   (1) a reaction step of hydrolyzing 5-[2-(methylthio)ethyl]imidazolidine-2,4-dione in the presence of a basic potassium compound;
   (2) a first crystallization step of introducing carbon dioxide into the reaction solution obtained in the step (1) to thereby precipitate methionine, and separating the resulting slurry into a precipitate and a mother liquor;
   (3) a second crystallization step of concentrating the mother liquor obtained in the step (2), mixing the resulting concentrate with a lower alcohol, introducing carbon dioxide into the resulting mixture to thereby precipitate methionine and potassium hydrogencarbonate, and separating the resulting slurry into a precipitate and a mother liquor; and
   (4) a heating step of concentrating the mother liquor obtained in the step (3), treating the resulting concentrate by heating at a temperature of from 150 to 200° C., and recycling the treated solution for use in the step (2).

2. The process of claim 1, wherein the lower alcohol used in the step (3) is selected from methyl alcohol, ethyl alcohol, n-propyl alcohol, isopropyl alcohol and t-butyl alcohol.

3. The process of claim 1, wherein the heat treatment is continued for 0.3 to 10 hours in the step (4).

4. The process of claim 2, wherein the heat treatment is continued for 0.3 to 10 hours in the step (4).

* * * * *